United States Patent [19]

Mathus

[11] Patent Number: 5,508,005

[45] Date of Patent: Apr. 16, 1996

[54] NON-SCREECHING LABORATORY ARTICLE

[75] Inventor: Gregory Mathus, Concord, Mass.

[73] Assignee: Costar Corporation, Cambridge, Mass.

[21] Appl. No.: 142,520

[22] Filed: Oct. 26, 1993

[51] Int. Cl.[6] ........................................................ B01L 3/00
[52] U.S. Cl. .......................... 422/102; 422/99; 435/288.4; 435/305.2
[58] Field of Search ........................... 422/99, 102, 104; 436/809; 435/284, 287, 293, 297, 300, 301, 310

[56] References Cited

U.S. PATENT DOCUMENTS

| | | | |
|---|---|---|---|
| 3,649,464 | 3/1972 | Freeman | 435/284 |
| 3,863,426 | 2/1975 | Courvalin | 53/237 |
| 4,012,288 | 3/1977 | Lyman et al. | 435/284 |
| 4,319,841 | 3/1982 | Suovaniemi et al. | 435/301 X |
| 4,321,330 | 3/1982 | Baker et al. | 435/300 X |
| 4,349,632 | 9/1982 | Lyman et al. | 435/284 |
| 4,822,741 | 4/1989 | Banes | 435/300 |
| 4,824,791 | 4/1989 | Ekholm et al. | 422/102 X |
| 4,968,625 | 11/1990 | Smith et al. | 435/301 |
| 5,096,672 | 3/1992 | Tervamäki et al. | 422/102 |
| 5,100,626 | 3/1992 | Levin | 422/101 X |

*Primary Examiner*—James C. Housel
*Assistant Examiner*—Maureen M. Wallenhorst
*Attorney, Agent, or Firm*—Wolf, Greenfield & Sacks

[57] ABSTRACT

A laboratory article, and in particular a cluster plate is provided including a plurality of wells supported by a structural framework including a peripheral wall. At locations in the structural framework a plurality of protrusions are provided so as to support the cluster plate on a support surface, such as a benchtop, in a point-to-point manner. Such point-to-point support allows the article to be moved across the support surface without the generation of unpleasant audible vibrations. According to a preferred embodiment, a cluster plate having protrusions extending from the lower edge of a peripheral wall is provided.

23 Claims, 6 Drawing Sheets

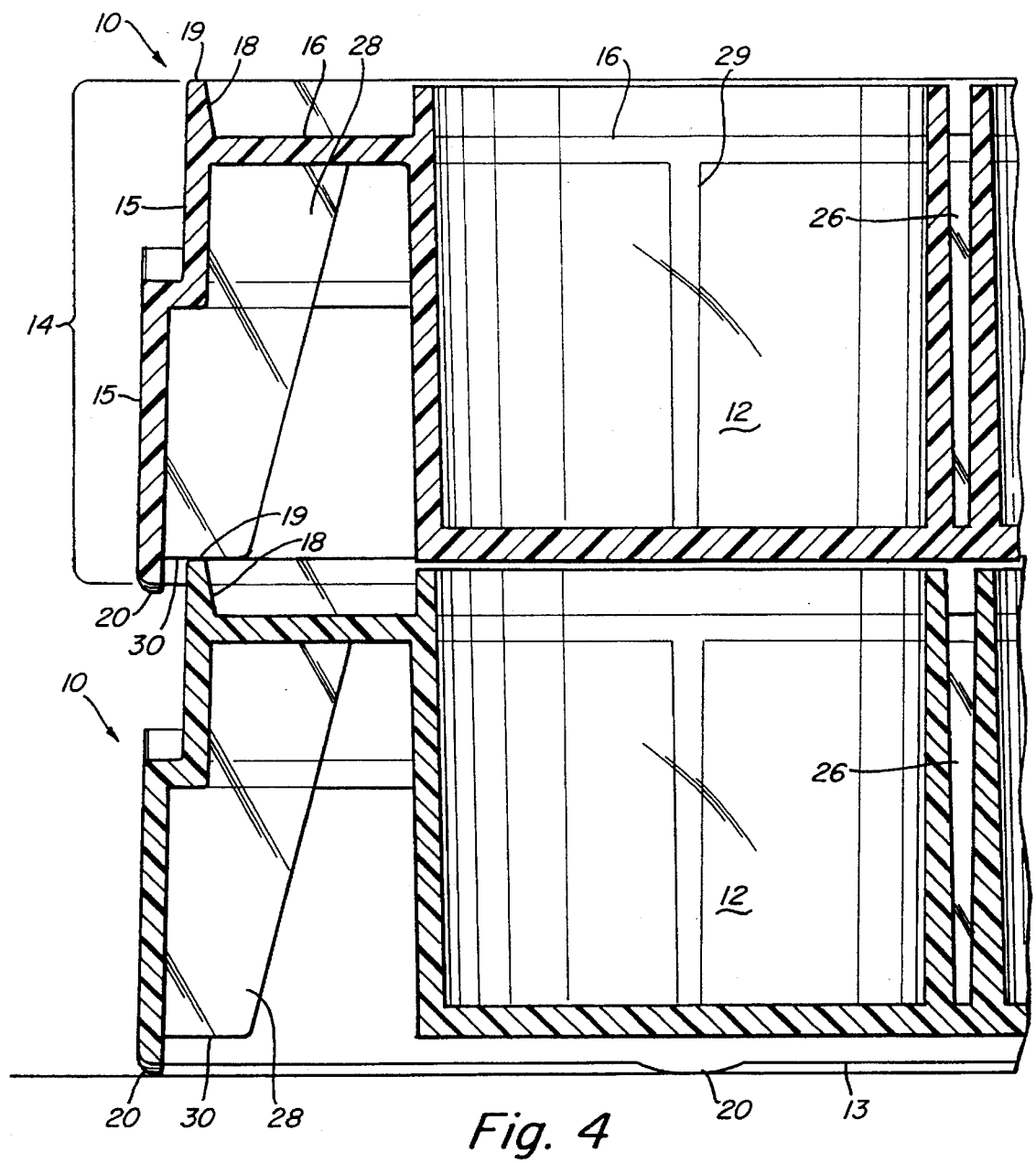
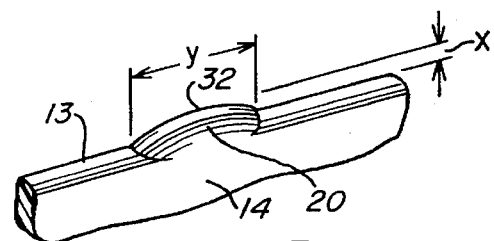
Fig. 4
Fig. 5

NON-SCREECHING LABORATORY ARTICLE

FIELD OF THE INVENTION

The present invention relates generally to a laboratory article designed to slide across a supporting surface without emitting unpleasant audible vibrations, and more particularly to a cluster plate including a plurality of protrusions positioned to support the plate in spaced relation from a supporting surface.

BACKGROUND OF THE INVENTION

In the field of chemistry and biology, numerous small, light-weight articles exist for supporting laboratory apparatus, storing laboratory reagents, or in which micro-chemical or micro-biological reactions or assays may be carried out. Exemplary of such an article is a cluster plate, typically comprising a one-piece molded plastic article having a plurality of test wells interconnected through a supporting structural framework, the framework including a free-standing peripheral wall. Typically, the cluster plate is fabricated such that the lower edge of the peripheral wall supports the remainder of the plate in spaced relation from a laboratory benchtop.

As used herein, the terms "free-standing peripheral wall" and "free-standing substantially planar portion" are meant to define substantially planar components or sections of a laboratory article, at least one portion of which lacks rigid support to the extent that friction generated between the portion, usually an edge of the portion, and a surface along which it is moved causes unpleasant audible vibrations. Such vibrations are generally thought to be the result of undamped vibration of the substantially planar portion. However, the vibrations causing the unpleasant audible sounds may be the result of, or further compounded by, resonance within the entire laboratory article, or from vibrations of sections of the article other than the planar portions. Typical of such unpleasant audible vibrations is the high-pitched screeching sound associated with movement of a cluster plate across a laboratory benchtop. Certain persons find such vibrations so irritating that physical effects are felt.

Therefore, there is a need in the art of laboratory chemistry and biology for a laboratory article which may be caused to slide across a surface such as a benchtop without emitting unpleasant, high-pitched audible vibrations.

Accordingly, a general purpose of the present invention is to provide a laboratory article designed to rest on a surface in such a way that any substantially planar portions of the article are supported in spaced relation from the surface, so that they are not caused to vibrate excessively when the article is moved across the surface.

SUMMARY OF THE INVENTION

The foregoing and other objects and advantages of the present invention are achieved by providing a microchemical laboratory article designed to rest on a surface, the article comprising a structural framework including free-standing, substantially planar portions, and a plurality of protrusions on the article positioned to support the substantially planar portions in spaced relation from the surface. The substantially planar portions may comprise a peripheral wall integral with the structural framework, the framework also including reinforcing ribs and a plurality of test wells supported by the framework. The protrusions may be integral with the overall article, or may be attached to a preformed article, and may be on the bottom of the test wells, on the lower portions of reinforcing ribs, along the lower edges of the peripheral wall or any combination of the above.

According to another embodiment of the present invention a cluster plate designed to rest on a surface is provided, comprising a plurality of wells interconnected through a structural framework, the framework including free-standing, substantially planar portions and a plurality of protrusions on the plate positioned to support the substantially planar portions in spaced relation from the surface. The structural framework generally includes the wells, a peripheral wall, and reinforcing ribs supporting the wall, and the protrusions may be positioned on bottoms of the wells, on lower portions of the reinforcing ribs, on the lower edge of the peripheral wall, or any combination of the above.

According to a preferred embodiment of the present invention a cluster plate is provided comprising a peripheral wall having a substantially rectangular cross-section connected to a plurality of wells and positioned so as to support the wells in spaced relation from a supporting surface, and a plurality of protrusions on the lower edge of the wall positioned to support the edge of the wall in spaced relation from the supporting surface.

Other advantages, novel features and objects of the invention will become apparent from the following detailed description of the invention when considered in conjunction with the accompanying drawings.

BRIEF DESCRIPTION OF THE DRAWINGS

In the drawings:

FIG. 4 is a cross-sectional view taken along section line 4—4 of FIG. 2, including a second cluster plate stacked upon the cluster plate illustrated in FIG. 2;

FIG. 5 is a fragmentary bottom perspective view of the embodiment illustrated in FIG. 1;

DETAILED DESCRIPTION OF THE PREFERRED EMBODIMENT

The present invention provides for a laboratory article designed to rest on a supporting surface, and designed and constructed so as to be movable across the supporting surface without emitting unpleasant audible vibrations. The inventive laboratory article may take a variety of forms, including but not limited to apparatus for supporting test tubes, pipettes or other chemical or biological laboratory apparatus, petri dishes, microchemical reaction test or test assay supporting surfaces, and the like. The preferred article is a cluster plate including a plurality of wells in which individual chemical or biological reactions may be effected.

The inventive laboratory article may be constructed by assembling individual components, or may be constructed as a one-piece unit. Particular materials used for fabrication of the inventive laboratory article, and the method of assembly if assembly is required, is not important to the present invention. The inventive laboratory article may be formed from a variety of materials including polymeric material, glass, ceramic, carbon fiber, and the like. It is simply advantageous that the particular material be selected to be compatible with respect to any chemical or biological reaction or culture which is to be carried out with its use. Typically, the article is constructed as a one-piece unit, for example via injection molding of polymeric material such as a plastic. Such articles are inexpensively manufactured and may be constructed of disposable or recyclable material to produce a one-use article.

As discussed above, such articles typically include free-standing supporting walls which, when moved across a surface, emit unpleasant, high-pitched audible vibrations. Such vibrations are generally generated through friction created between the supporting surface and the edge of a free-standing substantially planar portion of the article that is in substantially perpendicular relation with the surface. Therefore, the present invention provides for a substantially point-to-point contact between the article and a supporting surface, rather than contact between the edge of a free-standing planar portion and a surface.

Such point-to-point contact provided by the present invention may take a variety of forms, a preferred form being the provision of protrusions extending from the lower extremities of the inventive laboratory article, the protrusions being integral with the article, separately formed and attached to the article, or formed on the article after article fabrication.

Figure 1:
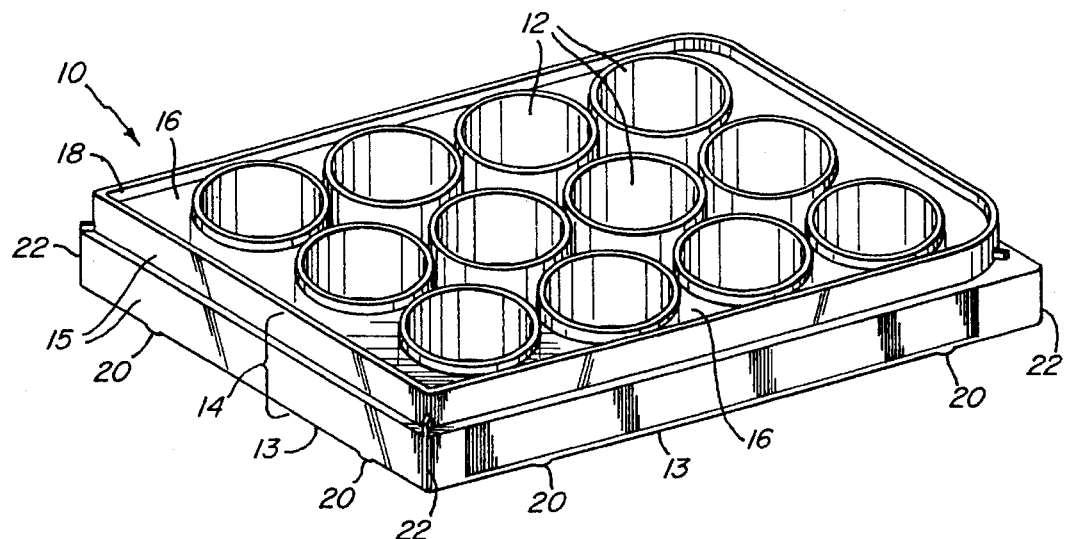
FIG. 1 is a perspective view of a cluster plate according to one embodiment of the present invention.

Referring now to FIG. 1, a laboratory article according to the present invention, specifically a cluster plate, is illustrated generally at 10 and comprises a plurality of wells 12 interconnected through a structural framework including free-standing, substantially planar portions 15 in the form of a peripheral wall 14 surrounding wells 12, the wall being constructed to be substantially perpendicular to a surface upon which the cluster plate rests, and wall-to-well connecting member 16. As illustrated, member 16 extends from wall 14 to connect wall 14 to the outermost wells of the cluster plate. However, plate 10 may be constructed such that member 16 interconnects all wells 12. The cluster plates of the invention illustrated herein are formed from clear plastic, as this may be advantageous when it is desirable to view any contents of wells 12.

As illustrated in FIG. 1, cluster plate 10 is constructed with a two-tiered wall 14 including lip 18 extending upwardly from wall 14. The two-tiered structure in concert with the lip provides for convenient stacking of a plurality of cluster plates 10.

According to the invention, cluster plate 10 includes a plurality of protrusions 20 extending downwardly from the plate so as to support the plate in a substantially point-to-point manner, that is, in a way such that substantially planar portions 15 are in spaced relation from a supporting surface. Illustrated in FIG. 1 is an embodiment in which peripheral wall 14 has a substantially rectangular horizontal cross-section having four sides, and the protrusions extend downwardly from lower edge 13 of the wall, two protrusions per side, resulting in a total of 8 points supporting the cluster plate. Alternately, one protrusion per side could be formed at the lower edge 13 of wall 14, and the cluster plate would be supported at 4 points. The particular number of protrusions, or supporting points, is not critical to the present invention. However, it is generally advantageous that a rectangular plate such as that illustrated in FIG. 1 is formed with protrusions relatively near corners 22 of the lower edges 13 of wall 14 as this adds stability to the cluster plates. If protrusions 20 are formed or attached at some distance from corners 22, for example midway between corners 22, the cluster plate may rock if pressure is applied thereto at locations near or above corners 22, and this may be disadvantageous in certain circumstances. In other circumstances such an arrangement may be advantageous, for example when it would be desirable to slightly rock the plate to agitate solutions in the wells in a controlled and reproducible manner.

Figure 2:
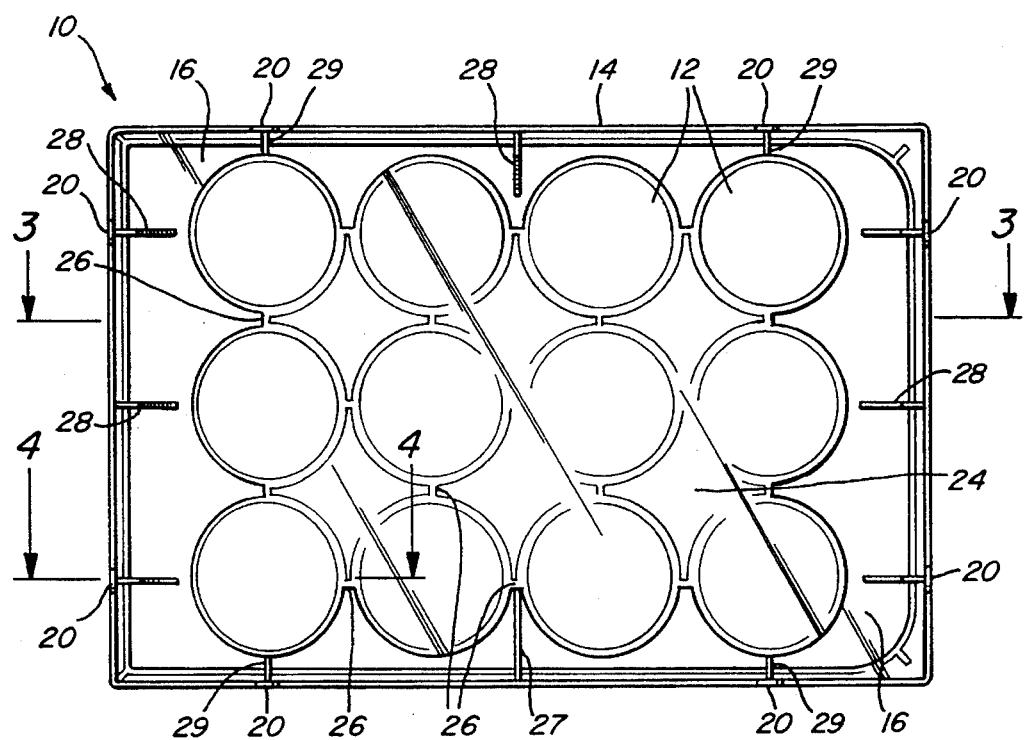
FIG. 2 is a bottom plan view of the cluster plate illustrated in FIG. 1.

Referring now to FIG. 2, a bottom plan view of cluster plate 10 is illustrated. In FIG. 2 and in other figures herein, elements common to various figures are represented by common numerical designations. In FIG. 2 well-to-well connecting member 24 and well-to-well connecting ribs 26 are illustrated. According to the embodiment illustrated, well-to-well connecting member 24 is a continuous planar member also defining the bottom walls of wells 12. Also illustrated in FIG. 2 are reinforcing ribs 28 adding structural support between wall 14 and wall-to-well connecting member 16, and wall-to-well reinforcing ribs 29. Additionally, supporting member 27 which connects wall 14 to well-to-well connecting rib 26 is illustrated. It is to be understood that any of ribs 28 as illustrated could extend to wells 12, or to well-to-well connecting members 26, and be fastened thereto, to add further structural support to the cluster plate.

Figure 3:
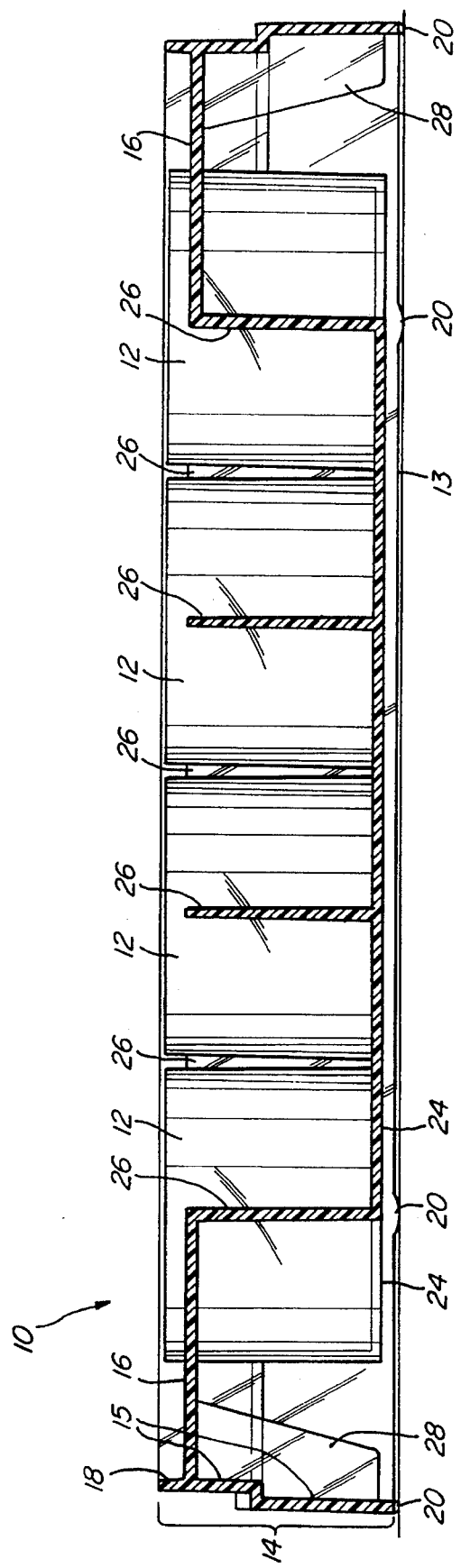
FIG. 3 is a cross-sectional view taken along section line 3—3 of FIG. 2.

FIG. 3 is a cross-sectional view taken along section 3—3 of FIG. 2, illustrating clearly the support given to wells 12 by well-to-wall connecting member 16 and well-to-well connecting member 24. Additionally, well-to-well connecting ribs 26 and reinforcing ribs 28 are clearly illustrated. Each reinforcing rib 28, in the embodiment illustrated in FIG. 3, is connected to well-to-wall connecting member 16 and wall 14 to provide structural support to these two elements.

Referring now to FIG. 4, the stackability of cluster plate 10 is illustrated. Reinforcing rib 28 includes lower edge 30, and lip 18 of wall 14 includes upper edge 19. As illustrated in FIG. 4, upper edge 19 of lip 18 of a first plate contacts lower edge 30 of reinforcing rib 28 of a second plate stacked on the first plate. When the cluster plates are stacked, lip 18 of the lower plate and wall 14 of the upper plate overlap to provide lateral stability. Additionally, lower edge 30 of reinforcing rib 28 and the upper edge 19 of lip 18 are designed so that when two plates are stacked, wells 12 of the individual plates are separated slightly from each other. Also clearly illustrated in FIG. 4 is the interconnection of well-to-well connecting member 16 and wall-to-well rib connectors 29. According to a preferred embodiment, members 16 and connectors 29 are integral.

Referring now to FIG. 5, a fragmentary bottom perspective of a section of edge 13 of wall 14 is illustrated, showing protrusion 20 in detail. Protrusion 20 may take a variety of forms, as long as a substantially point-to-point support of cluster plate 10 is realized. Typically, protrusion 20 extends at least three thousandths of an inch from edge 13 of wall 14 (dimension x in FIG. 4). More typically, protrusion 20 extends at least six thousandths of an inch from edge 13, or may extend ten thousandths of an inch or more from edge 13. The outward extension of protrusion 20 from edge 13 (dimension x) is advantageously uniform among the several protrusions 20, so that no rocking of the cluster plate occurs, and so that the cluster plate is retained in relatively parallel relation with the surface upon which it is supported.

The length of protrusion 20, that is, the extension along edge 13 of wall 14 from which protrusion 20 extends (dimension y in FIG. 5), may take a variety of dimensions. The length of protrusion 20 along edge 13 is not important to the present invention, so long as the outermost extension of protrusion 20 that contacts a supporting surface upon which plate 10 is rested, contact area 32, is small enough that movement of the cluster plate along a surface does not cause unpleasant high-pitched audible vibrations. For example, the length of protrusion 20 (dimension y) may equal anywhere from a few thousandths of an inch to one-half inch or more.

More important than the particular dimension of protrusion 20 is its shape. It is important that protrusion 20 is shaped such that a smooth transition exists between edge 13 of wall 14 and contact area 32 of protrusion 20. If the transition between edge 13 and contact area 32 is not smooth and blended but is relatively sharp, protrusion 20 may catch on non-smooth surfaces upon which the cluster plate is placed. For example, the typical laboratory includes grates, racks, and other structures that include discontinuities, within which a protrusion 20 could catch if it were not designed to include a smooth transition from edge 13 to contact area 32.

Figure 6:
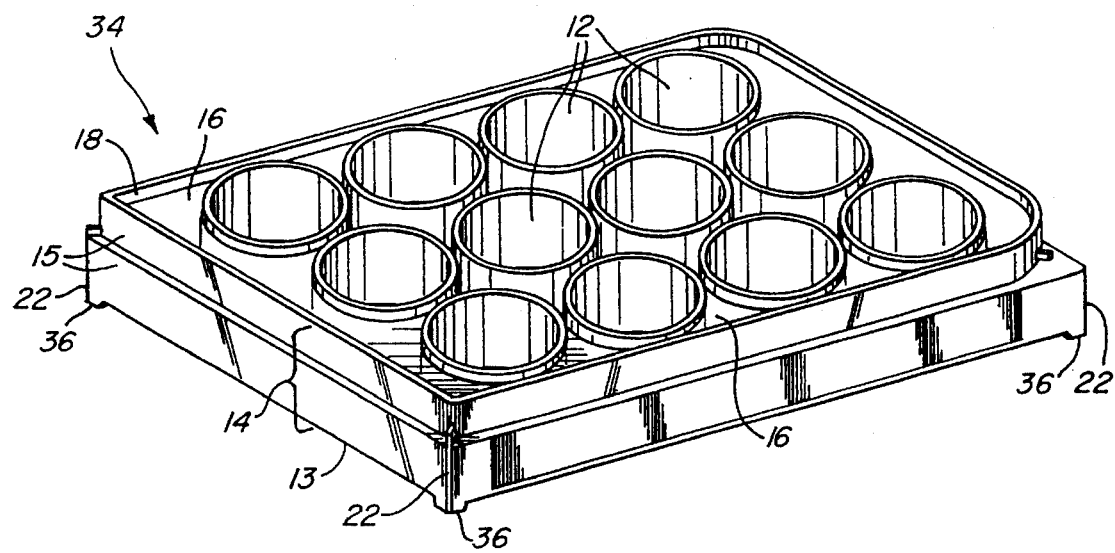
FIG. 6 is a perspective view of a cluster plate according to another embodiment of the present invention.
Figure 7:
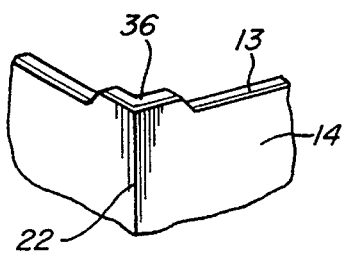
FIG. 7 is a fragmentary bottom perspective view of the embodiment illustrated in FIG. 6.

Referring now to FIG. 6, a cluster plate 34 according to another embodiment of the present invention is illustrated. Cluster plate 34 differs from cluster plate 10 in that cluster plate 34 includes protrusions 36 at corners 22 of wall 14, rather than at locations along the sides of wall 14 between the corners. A fragmentary bottom perspective of the region surrounding corner 22 of cluster plate 34 of FIG. 6 is illustrated in FIG. 7. Cluster plate 34 is designed, as is cluster plate 10, to be movable along a supporting surface without emitting unpleasant high-pitched audible vibrations. An added feature of cluster plate 34 is greater stability; downward pressure on any portion of cluster plate 34 does not result in rocking or teetering of cluster plate 34 on a surface upon which it is supported.

Thus far, a laboratory article is described which has an outer peripheral wall including protrusions positioned on the edge of the wall to support the article such that the outer peripheral wall is in spaced relation from a supporting surface. According to the embodiments discussed and illustrated thus far, protrusions 20 are positioned along edge 13 of wall 14 at locations where wall 14 is reinforced. What is meant by reinforced portions of wall 14 include areas of wall 14 at or near an intersection of the wall with a corner 22, a wall-to-well reinforcing rib 29, a reinforcing rib 28, at a supporting member 27, etc., that is, portions of wall 14 that are not free standing. For example, with reference to FIG. 2, protrusions 20 are positioned along edge 13 of wall 14 at locations where reinforcing ribs 28 and wall-to-well reinforcing ribs 29 meet wall 14. With reference to FIG. 6, protrusions 36 are positioned at corners 22 of cluster plate 34. According to these preferred embodiments in which protrusions 20 or 36 are positioned along wall 14 at reinforced portions thereof, vibrations of planar portions 15 of wall 14 are minimized when the article is moved across a supporting surface. This is due to the fact that any vibration transferred from the supporting surface, through the protrusion, to the wall 14 upon movement of the article across the surface is immediately damped by the reinforced corners, ribs, or the like. If the protrusions were positioned along a free-standing substantially planar portion 15 of wall 14, for example, with reference to FIG. 2, midway between a wall-to-well reinforcing rib 29 and a reinforcing rib 28, sliding vibration would be transferred to free-standing portions 15 of wall 14, increasing audible vibrations.

Figure 8:
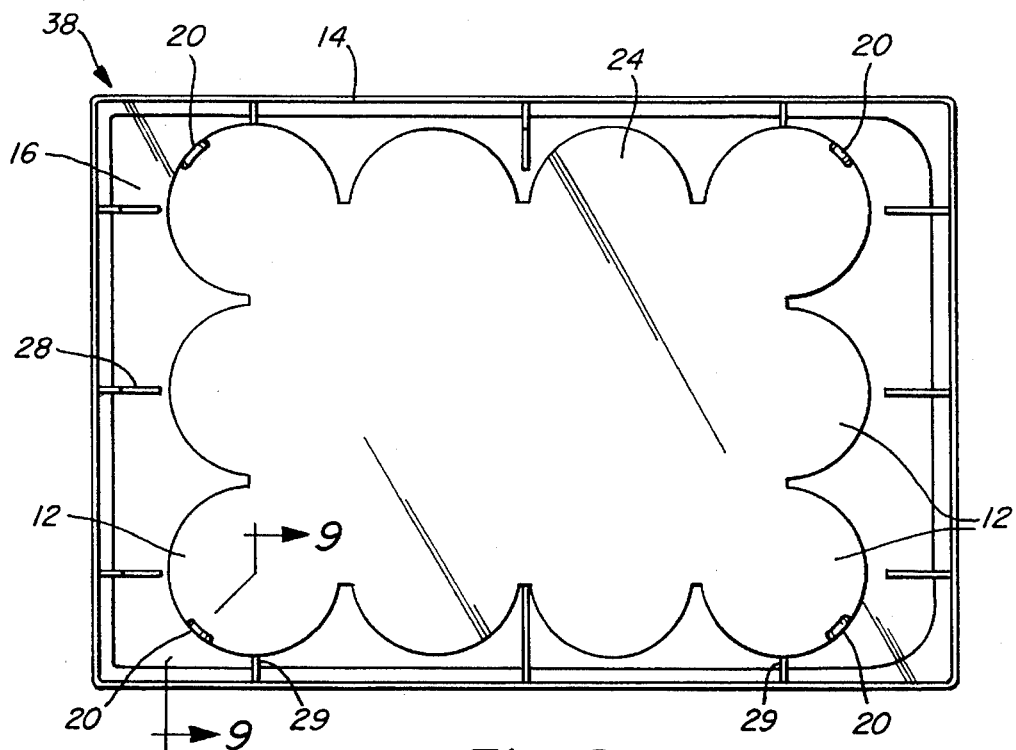
FIG. 8 is a schematic bottom plan view of a cluster plate according to another embodiment of the present invention.

According to the embodiments described thus far, the inventive protrusions are positioned on an outer peripheral wall of a laboratory article. However, such protrusions need not be confined to the outer peripheral wall, but may be positioned anywhere on the article such that the article is supported in a way that portions which may contribute to unpleasant audible vibrations when dragged along a supporting surface are in non-contacting relation with the supporting surface. Such an alternate embodiment is illustrated in FIG. 8. As illustrated, cluster plate 38 includes protrusions 20 on the bottom portions of wells 12. Protrusions 20 are constructed so as to extend from the bottom portions of wells 12 to the extent that other portions of cluster plate 38 are supported in non-contacting relation with the supporting surface. According to the preferred embodiment of cluster plate 38 illustrated, protrusions 20 of are provided on the bottom portions of the wells 12 which define corner wells of the cluster plate well matrix, providing good stability.

Figure 9:
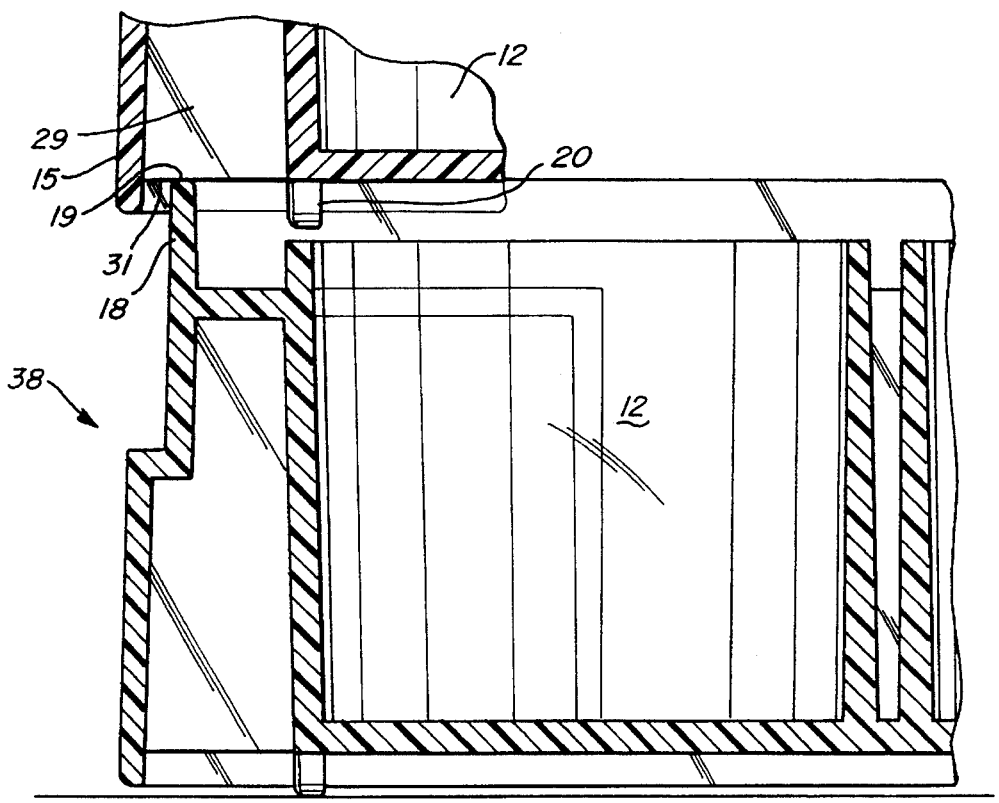
FIG. 9 is a cross-sectional view taken along section line 9—9 of FIG. 8, including a second cluster plate stacked upon the cluster plate illustrated in FIG. 8.

Referring now to FIG. 9, features of cluster plate 38 are illustrated which allow stacking of cluster plates according to the embodiment of FIG. 8 without contact between wells 12 of a bottom plate and protrusions 20 of a plate stacked upon the bottom plate. According to this embodiment, cluster plate 38 includes lip 18 which extends upwardly farther than lip 18 of cluster plate 10. Upper portion 19 of lip 18 contacts lower portion 31 of wall-to-well reinforcing rib 29 of another cluster plate 38 stacked upon it, holding the cluster plates in a way that wells 12 of the lower plate do not contact protrusions 20 of the upper plate.

Figure 10:
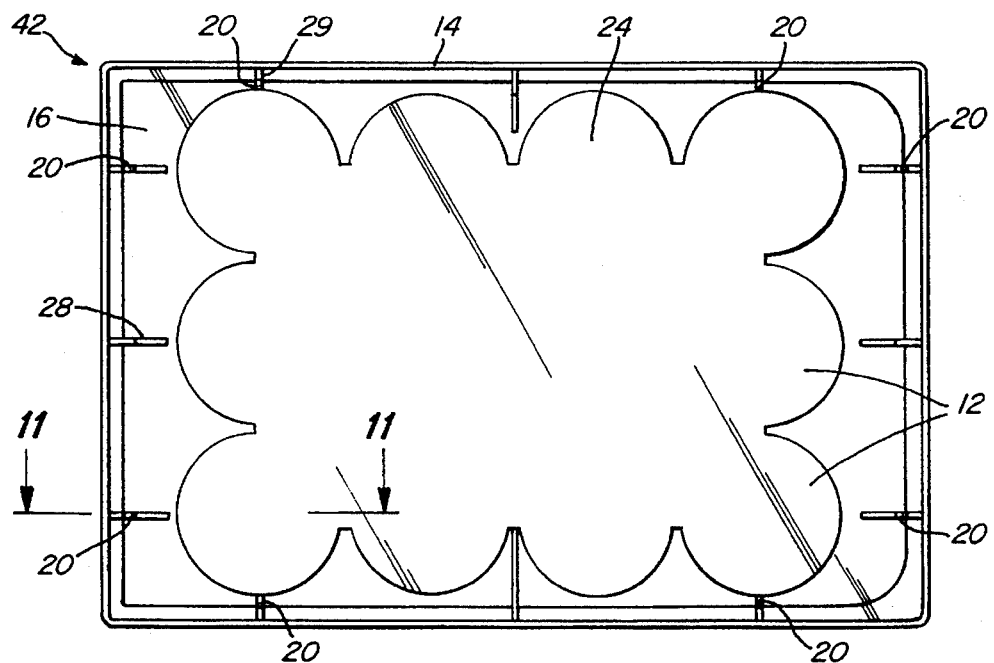
FIG. 10 is a schematic bottom plan view of a cluster plate according to yet another embodiment of the present invention.
Figure 11:
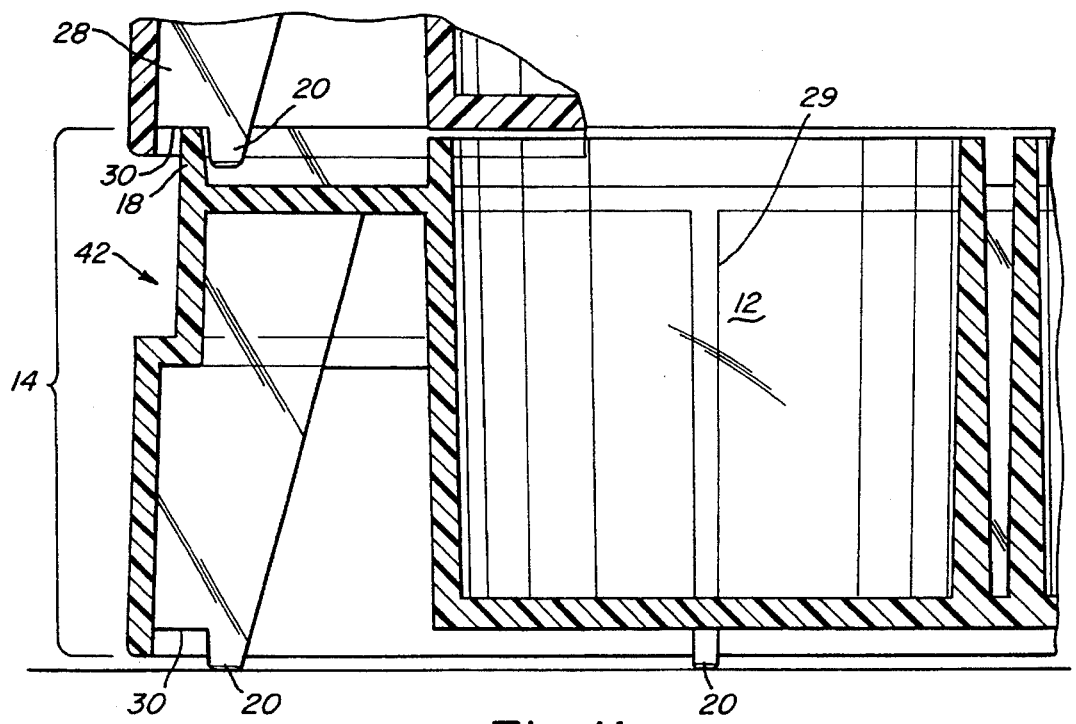
FIG. 11 is a cross-sectional view taken along section line 11—11 of FIG. 10, including a second cluster plate stacked upon the cluster plate illustrated in FIG. 10.

According to yet another embodiment, and with reference to FIG. 10, cluster plate 42 is illustrated in which protrusions 20 extend from bottom edges 30 of reinforcing ribs 28 and from the bottom edges of wall-to-well reinforcing ribs 29. FIG. 11 is a cross-sectional view taken along section 11—11 of FIG. 10, illustrating the stackability of cluster plates 42. An additional feature of this embodiment is that the lateral tolerance between protrusion 20 of the upper stacked plate and lip 18 of wall 14 of the lower stacked plate is small, adding lateral stability to cluster plates stacked in this way.

It is to be understood, with reference to FIGS. 8–11, that cluster plates 38 and 42 are advantageously fabricated such that a plurality of protrusions 20 may be provided in any number and positioned in any way, so long as the cluster plates are supported on a surface in a relatively stable manner. These and other embodiments in which a laboratory article such as a cluster plate is supported in a point-to-point relation on a supporting surface, for example via the protrusions described herein, are within the scope of the present invention. It is noted, especially with respect to FIG. 9, that lip 18 may be adjusted to accommodate protrusions at various locations of the cluster plate while maintaining the ability to stack the plates with wells of the plates in non-contacting relation with wells of others of the plates.

As discussed above, protrusions 20 may be integral with the laboratory article of the invention. That is, in the manufacturing process a one-piece article may be fabricated including protrusions 20, or one component of the article, such as an individual side of wall 14, may be fabricated with protrusions 20 integral therewith. Alternately, the article may be fabricated as a unit without protrusions, and protrusions may be added subsequently. Such addition may be made by fastening protrusion 20 to edge 13 of wall 14, or to other portions of the article, with adhesive or other known fastening means. According to the latter embodiment, protrusions 20 may or may not comprise the same material that is used to fabricate other portions of the article.

Illustrated thus far in accordance with the above description is a cluster plate having 12 wells. However, the cluster plate of the present invention may comprise a variety of configurations. For example, 6-well, 12-well, 24-well, 48-well, 96-well, and 192-well configurations may be fabricated, and these and other configurations are within the scope of the present invention.

Also provided in accordance with the present invention is a method of reducing audible vibrations associated with the movement of laboratory apparatus, such as cluster plate 10, across a supporting surface. According to the method, an existing article, such as a cluster plate, may be modified to include protrusions 20. For example, protrusions 20 may be fastened to an existing article with adhesive or other known fastening means.

Those skilled in the art will readily appreciate that all elements and parameters listed herein are meant to be exemplary and that actual elements and parameters will depend upon the specific application for which the laboratory article is to be employed. For example, a rectangular cluster plate is exclusively illustrated, but cluster plates or other articles having other shapes such as circles, triangles, and the like could be constructed in accordance with the present invention and are understood to be within its scope. It is, therefore, to be understood that the foregoing embodiments are presented by way of example only and that, within the scope of the appended claims and equivalents thereto, the invention may be practiced otherwise than is specifically described.

What is claimed is:

1. An article comprising: a cluster plate having a peripheral wall forming a downwardly facing open space and having a substantially rectangular cross-section connected to a plurality of open wells and positioned so as to support said wells in spaced relation from a supporting surface, said wall having a lower edge; and a plurality of protrusions on said lower edge positioned to support said edge in spaced relation from said supporting surface for preventing audible vibrations of the peripheral wall when the plate is slid across a work surface.

2. The cluster plate as recited in claim 1, said peripheral wall having four corners at said lower edge, and said plate comprising one protrusion positioned on said lower edge of said peripheral wall at each corner.

3. The cluster plate as recited in claim 1, said peripheral wall having four sides, and said plate comprising at least one protrusion along each side of said wall at said lower edge.

4. The cluster plate as recited in claim 3, said peripheral wall having four corners at said lower edge, each of said corners defining the junction of two of said sides of said peripheral wall, said plate comprising two protrusions along each side of said peripheral wall at said lower edge, each of said protrusions being spaced approximately equidistantly between the center of one of said sides and one of said corners.

5. The cluster plate as recited in claim 1, wherein said protrusions are integral with said lower edge.

6. The cluster plate as recited in claim 1, wherein said protrusions are attached to said lower edge.

7. The cluster plate as recited in claim 1, selected from the group consisting of 6-well plates, 12-well plates, 24-well plates, 48-well plates, 96-well plates, and 192-well plates.

8. The cluster plate as recited in claim 1, further comprising a connector connecting said wells to said peripheral wall, and reinforcing ribs extending between said peripheral wall and said connector or said wells, wherein said plurality of protrusions are positioned on said lower edge of said wall at positions thereof where said reinforcing ribs are connected thereto.

9. The cluster plate as recited in claim 1, each of said plurality of protrusions including a contact area defined by the portion of each protrusion which extends furthest downwardly and which contacts said supporting surface, at least one of said protrusions shaped such that a smooth transition exists between said lower edge of said peripheral wall and said contact area.

10. The cluster plate as recited in claim 1, wherein said plurality of protrusions are constructed and arranged to support said cluster plate in a point-to-point manner on said supporting surface.

11. The cluster plate as recited in claim 1, wherein said wells are arranged in rows and columns within said rectangular cross section of said peripheral wall.

12. A cluster plate designed to rest on a surface, comprising:

a structural framework including a substantially horizontal connecting member having a plurality of open wells located therein, free-standing, substantially planar portions connected to said connecting member, said planar portions defining a peripheral wall of said structural framework and forming a downwardly-facing open space; and a plurality of protrusions on said plate positioned to support said substantially planar portions in spaced relation from said surface for preventing audible vibrations of the peripheral wall defined by the planar portions when the plate is slid across a work surface.

13. The cluster plate as recited in claim wherein said connecting member connects said wells to said peripheral wall, and wherein said structural framework further comprises reinforcing ribs extending between said peripheral wall and said connecting member or said wells.

14. The cluster plate as recited in claim 13, said wells each having a bottom, said protrusions positioned on a plurality of said well bottoms.

15. The cluster plate as recited in claim 13, said protrusions positioned on a plurality of said reinforcing ribs.

16. The cluster plate as recited in claim 13, said peripheral wall having a lower edge, and said protrusions positioned on said lower edge.

17. The cluster plate as recited in claim 16, said lower edge defining a rectangle having four corners, and said plate comprising one protrusion at each corner.

18. The cluster plate as recited in claim 16, said peripheral wall having four sides defining a substantially rectangular cross section, and said plate comprising at least one protrusion along each side of said wall at said lower edge.

19. The cluster plate as recited in claim 13, wherein said peripheral wall has a substantially rectangular cross section and said wells are arranged in rows and columns within said rectangular cross section of said peripheral wall.

20. A microchemical laboratory article designed to rest on a surface, comprising:

a structural framework including a connecting member having a plurality of open wells located therein, freestanding, substantially planar portions downwardly extending from said connecting member, said planar portions defining a peripheral wall of said structural framework and forming a downwardly facing open space; and a plurality of protrusions on said peripheral wall positioned to support said substantially planar portions in spaced relation from said surface for preventing audible vibrations of the peripheral wall when the article is slid across a work surface.

21. The laboratory article as recited in claim 20, wherein said connecting member connects said wells to said peripheral wall, and wherein said structural framework further comprises reinforcing ribs extending between said peripheral wall and said connecting member or said wells.

22. The laboratory article as recited in claim 21, said peripheral wall having a lower edge, and said protrusions positioned on said lower edge.

23. The laboratory article as recited in claim 21, wherein said peripheral wall has a substantially rectangular cross section and said wells are arranged in rows and columns within said rectangular cross section of said peripheral wall.

* * * * *